United States Patent [19]

Guiducci et al.

[11] 3,987,014

[45] Oct. 19, 1976

[54] SECRETIN INTERMEDIATES AND DERIVATIVES

[75] Inventors: Mariano Guiducci, Edison, N.J.; Roger Piasio, Medfield, Mass.

[73] Assignee: Becton, Dickinson and Company, Rutherford, N.J.

[22] Filed: Jan. 10, 1974

[21] Appl. No.: 432,180

[52] U.S. Cl. .................... 260/78 A; 260/112.5 R; 424/1
[51] Int. Cl.[2] .................. C07C 103/52; C07G 7/00
[58] Field of Search ............... 260/112.5, 112, 78 A

[56] References Cited
UNITED STATES PATENTS 3,812,091  5/1974  Ondetti ..................... 260/112.5

OTHER PUBLICATIONS

Bodansky et al., J. Am. Chem. Soc., 91, 944–949 (1969).

Bodanszky et al., J. Am. Chem. Soc., 89, 6753–6757 (1967).

Bodanszky et al., J. Am. Chem. Soc., 89, 685–689 (1967).

Bayer et al., Hoppe–Seyler's Zeit. Physiol. Chem., 352, 759–760 (1971).

J. M. Stewart and J. D. Young, "Solid Phase Peptide Synthesis," Freeman and Co., San Francisco (1969), pp. 1–13.

Pietta et al.: Chem. Comm., 1970, 650–651.

*Primary Examiner*—Lewis Gotts
*Assistant Examiner*—Reginald J. Suyat
*Attorney, Agent, or Firm*—Marn & Jangarathis

[57] ABSTRACT

[6-TYR] Secretin is biologically active and can be radio-iodinated for use in the radioimmunoassay of secretin. The peptide can be produced by solid phase synthesis using benzhydrylamine resin as the support.

16 Claims, No Drawings

SECRETIN INTERMEDIATES AND DERIVATIVES

This invention relates to peptides, and more particularly to the peptide [6 - TYR] Secretin and supported peptides employed for the production of [6 - IVR] Secretin and porcine Secretin.

Porcine Secretin has the formula:

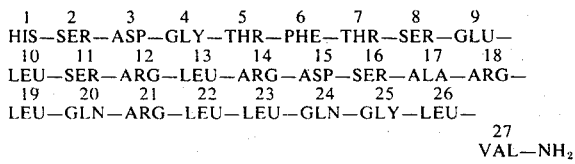

Accordingly, porcine secretin is a peptide containing 27 amino acid residues: L-Histidyl (HIS); L-Aspartyl (ASP); L-Seryl (SER); Glycyl (GLY); L-Threonyl (THR); L-Phenylalanyl (PHE); L-Glutamyl (GLU); L-Glutaminyl (GLN); L-Leucyl (LEU); L-Arginyl (ARG); L-Alanyl (ALA); and L-Valyl (VAL). In accordance with the present invention, there is provided a novel analogs of porcine Secretin in which tyrosine (TYR) replaces phenylalanine (PHE), hereinafter referred to as [6 - TYR] Secretin.

In accordance with another aspect of the present invention, there is provided radioiodinated [6 - TYR] Secretin.

In accordance with a further aspect of the present invention, there is provided novel intermediates for the production of both porcine and [6 - TYR] Secretin comprised of the amino acid moieties used in the preparation of both porcine Secretin and 6 [TYR] Secretin linked to a benzhydryl amine resin support, and characterized by the following structural formula:

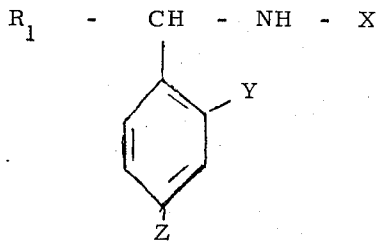

wherein $R_1$ is a solid polymer which is either polystyrene or polystyrene crosslinked with divinyl benzene, with the polymer being linked through a phenyl group, i.e., $R_1$ is

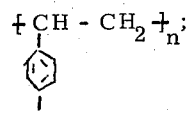

Y is either hydrogen or lower alkoxy (1-5 carbon atoms), preferably hydrogen;

Z is either hydrogen, lower alkoxy or nitro; and

X is either the protected or unprotected peptides or salts thereof comprised of from 1 to 27 amino acid residues, in sequence which are included in the peptide porcine Secretin or [6 - TYR] Secretin.

The peptide salts, include, for instance hydrochlorides, hydrobromides, acetates, trifluoroacetates hydrofluoride and chloroacetates, etc.

The novel peptide [6 - Tyr] Secretin and the novel peptide intermediates used in the production of the novel peptide or the peptide, porcine Secretin, are prepared by the solid phase technique, as generally disclosed by Merrifield; JACS, 85, 2149 (1963), using the hereinabove described benzhydrylamine resin as the solid support. The benzhydrylamine resin used in the present invention is described by Pieta et al., Chem. Comm., 650 (1970); and Rivier et al., J. Med. Chem., 16, 545 (1973). In accordance with the Merrifield technique, the first amino acid of the sequence (L-valine), which has its amino group protected, is linked to the resin support through its carboxyl group. The amino group of the first amino acid is then deprotected and the protected second amino acid is linked thereto. The sequence of deprotection and linking of amino acid is repeated until the desired peptide is formed. At this point, the peptide is deprotected and removed from the polymer support, as the amide of the C-terminal acid (the amide of L-valine).

In forming the amino acid sequences, the amino groups may be protected by any of the well-known protecting groups, such as, benzyloxycarbonyl, biphenylisopropyloxycarboxyl, t-amyloxycarbonyl, t-butyloxycarbonyl, phthalyl, o-nitrophenyl-sulfenyl, diisopropyloxycarbonyl, trityl, trifluoroacetyl, acetyl, tosyl, etc. The carboxyl group may also be protected by any one of the known protecting groups, such as, diphenylmethoxy, p-nitrophenoxy, cyanomethoxy, methoxy, ethoxy and t-butoxy, benzyloxy, etc.

In accordance with the preferred embodiment of the present invention, the peptide synthesis is initiated by attaching the c-terminal valine moiety to the benzhydrylamine resin by normal coupling techniques. The peptide chain is then lengthened by coupling the amino acids in the required sequence by normal coupling techniques. The protecting groups for the various amino acids are as follows: nitro for guanidine of arginine; benzyl esters for the aspartic and glutamic acids; benzyl ethers for the serine, threonine and tyrosine hydroxyl functions; benzyl and dinitrophenyl for imidazole of histidine; while glutamine was unprotected and coupled as the active paranitrophenyl ester. The coupling is effected using dicyclohexylcarbodiimide as the coupling agent and deprotection is effected with trifluororacetic acid in methylene chloride. When the synthesis is completed, the peptide is removed from the resin support with hydrofluoric acid, which simultaneously removes the blocking groups.

Secretin and the 6-tyrosyl analog are purified by ion exchange chromatography on SP Sephadex by gradient and stepwise elution, as described by E. Wunsch et al., Chem., Ber., 105, 2515 (1972).

The invention will be further described with respect to the following examples which illustrates a method for preparing [6-TYR] Secretin and its intermediates. Unless otherwise indicated all parts and percentages are by weight and all temperatures are in ° C.

EXAMPLE I

Benzhydrylamine resin (20g) (produced from 1% crosslinked divinylbenzene polystyrene resin beads) is transferred to the peptide reactor vessel of an automated peptide synthesizer, sold by Schwarz/Mann. The following solvents and reagents are prepared and transferred to the appropriate reservoirs of the synthesizer.

Reagent:

50% Trifluoroacetic acid (TFA) in methylene chloride (v/v)
Chloroform
10% triethylamine (TEA) in chloroform (v/v)
Methylene chloride
Dicyclohexylcarbodiimide (DCC)
Dimethylformamide (DMF)
Tertiarybutyloxycarbonyl-L-valine
Tertiarybutyloxycarbonyl-L-leucine
Tertiarybutyloxycarbonyl-glycine
Tertiarybutyloxycarbonyl-L-glutamine p-nitrophenyl ester
Tertiarybutyloxycarbonyl-nitro-L-arginine
Tertiarybutyloxycarbonyl-L-alanine
Tertiarybutyloxycarbonyl-O-Benzyl-L-serine
Tertiarybutyloxycarbonyl-β-benzyl-L-aspartate
Tertiarybutyloxycarbonyl-γ-benzyl-L-glutamate
Tertiarybutyloxycarbonyl-O-benzyl-L-threonine
Tertiarybutyloxycarbonyl-O-benzyl-L-tyrosine
Tertiarybutyloxycarbonyl-imidazole-dinitrophenyl-L-histidine
Tertiarybutyloxycarbonyl-glycine p-nitrophenyl ester
Tertiarybutyloxycarbonyl-O-benzyl-L-serine p-nitrophenyl ester
Tertiarybutyloxycarbonyl-β-benzyl-L-aspartate p-nitrophenyl ester A solution of tertiarybutyloxycarbonyl-L-valine (13.02 grams, 60mMole) in methylene chloride (400 ml) is transferred to the appropriate reservoir in the synthesizer. Each succeeding amino acid (60mMole) is dissolved in methylene chloride with the exception of the p-nitrophenyl esters and nitroarginine which require dimethylformamide for complete solution. The cycle for the incorporation of each amino acid into the growing peptide chain involves the following washing and reaction steps:
1. 3 washings with methylene chloride for 30 seconds.
2. A washing with 50% trifluoroacetic acid in methylene chloride for 30 seconds.
3. Reaction with 50% trifluoroacetic acid in methylene chloride for 20 minutes.
4. 4 washings with methylene chloride for 30 seconds.
5. 3 washings with chloroform for 30 seconds.
6. A washing with 10% triethylamine in chloroform for 30 seconds.
7. A washing with 10% triethylamine in chloroform for 5 minutes.
8. 4 washings with chloroform for 30 seconds.
9. 5 washings with methylene chloride for 30 seconds.
10. Boc amino acid in solution for 10 minutes.
11. DCC in methylene chloride for 2 hours.
12. 2 rinses with methylene chloride for 30 seconds.
13. Repeat of steps 10, 11 and 12.

Each coupling is tested for completion by the ninhydrin test; Kaiser et al., Analytical Biochemistry, 34, 395 (1970). Only after the test is negative (all reactive free amine group had been coupled) does the synthesis continue, otherwise the coupling is repeated. The only changes in the cycle occur with the coupling of p-nitrophenyl ester where step 11 is omitted. The amino acids are linked in the sequence required for producing [6 - Tyr] Secretin.

Thiolysis:

Removal of Dinitrophenol (DNP) protecting group from the imidazole ring of Histidine.

1. Thiolysis is done in a fume hood. Place 20 gms of peptide resin ester into a 1 liter Erlenmeyer flask.
2. 950 ml. DMF and 50 ml TEA are added with stirring. Then add 20 ml. of β-mercaptoethanol.
3. After one minute, stop the stirring. Take 25 λ of the supernatent and dilute with 2 ml. of 5% TEA/DMF (v/v). Start the reactor stirring as soon as possible.
4. Read the dilution against a 5% TEA/DMF blank by UV at 320, 340, 350 and 360 mμ. A maximum absorbance reads at 340 mμ.
5. Repeat steps Nos. 3 and 4 every 5 minutes. After approximately 35 minutes, the maximum at 340 m begin to level off and actually decrease. When this occurs, the reaction is complete. Filter immediately onto a sintered glass funnel with aspiration.
6. Wash resin well with DMF, methylene chloride, 50% TFA in methylene chloride solution and methylene chloride. Dry the resin overnight in a vacuum oven.

Cleavage:
1. Take 5 gms of the peptide resin ester and place into a large KEL-F reactor vessel with a magnetic stirring bar.
2. Add 10 ml of anisole.
3. Transfer 50 ml. of hydrofluoric acid (HF) into the reactor vessel. Stir at 0° C. for 1 hour.
4. Remove HF from the reactor vessel via a water aspirator. When all of the HF is removed, transfer to a high vacuum pump to remove the last traces of HF and anisole.
5. Remove the reactor vessel from the HF apparatus. Immediately fill with ethyl acetate. Filter onto a sintered glass funnel.
6. Wash well with ethyl acetate.
7. Extract the peptide with 0.2N acetic acid solution. Lyophilize.

Preliminary Purification:

DEAE Sephadex A-25 Column

1. Prepare a DEAE Sephadex A-25 (acetate form) column. Equilibrate with 10% aqueous acetic acid solution.
2. Dissolve 950 mg. of crude [6 -TYR] Secretin in 50 ml of 10% aqueous acetic acid solution.
3. Charge the column with 10% aqueous acetic acid solution. Collect approximately 200 ml. and lyophilize.

Purification:

Crude [6-TYR] Secretin (100 mg) is dissolved in 20 ml of an equal mixture of buffer solution (0.3 Molar $NH_4OAc$, pH 4.5) and $H_2O$. After filtration the pH of the filtrate is adjusted to 4.0 with acetic acid, and charged onto a Sephadex SP column (2.4 cm × 40 cm) previously equilibrated with the buffer solution (pH 4.5). Elution is effected with this buffer until ca. 10 bed volumes were collected and elution continued with a new buffer solution, pH 6.0 (0.3M ammonium acetate, 103 ml glacial acetic acid in 6 liter water (total volume) adjusted to pH 6.0 with ammonium hydroxide). 20 ml. fractions at a rate of 100 ml/hour are collected.

Reading:
Read O.D. at 230 mμ of every other tube. Plot the readings. Take aliquots (1 ml) of every other tube where peak is observed and evaporate overnight in oven. Add 0.15 ml of sodium hydroxide solution (13.5 N) and place in an autoclave for 20 min. Then add 0.25 ml of glacial acetic acid, 2 ml of ninhydrin buffer solution and 50 λ of stannous chloride solution. Heat this mixture for 15 minutes in a steam bath. Dilute with 10 ml of a 50% aqueous ethanol solution and read O.D. at 570 mμ on a Beckman DBG Spectrophotometer. Plot the readings and pool according to the observed peaks (tubes No. 19–26 after change of eluant from pH of 4.5 to 6.0). The pooled fractions are lyophilized and analyzed.

The peptide was identified as [6-TYR] Secretin by amino acid analysis and ultraviolet absorption.

[6-TYR] Secretin was found to be biologically active by the tests described by Jorpes et al; Acta. Chem. Scand. 15, 1970 (1961); Biochem. Biophys. Res. Commun. 9, 275 (1962); Biochem 4, 2358 (1965); and Fourth Int. Symp. Chem. Nat. Prod., Stockholm (1966).

Although the present invention has been particularly described with respect to the preparation of [6-TYR] Secretin by the preferred solid phase synthesis using a benzhydrylamine resin support, it is to be understood that the compound can be made by other procedures such as stepwise coupling of active esters or any other procedure known in the art.

[6-TYR] Secretin is biologically active and can be used for the same purposes and in the same manner as porcine secretin; for example, to stimulate bicarbonate flow, inhibit gastrin, etc., as disclosed in Handbuch at experimentellen, Phatmakoloji Series XXXIV. Spruyer Verlag Editors: Jorpes and Mutt.

[6-TYR] Secretin can be radioiodinated to produce radioiodinated [6-TYR] Secretin, with the radioiodination being effected with either $^{125}I$, $^{131}I$ or $^{123}I$, preferably $^{125}I$. [6-TYR] is radioiodinated (using $^{125}I$ as a representative tracer) to 6-($3^1$-iodo $^{125}I$-tyrosyl) secretin and 6-($3^1$, $5^1$-diiodo $^{125}I_2$-tyrosyl) secretin. The radioiodination is preferably effected by essentially the Hunter-Greenwood chloramine -T method [Nature 194, 495-96 (1962)], although other techniques; e.g., using lactoperoxidase [Thorell et al, Brochemica et Biophysica Acta 251, 363-69 (1971)], may also be employed.

The radioiodinated peptide of the present invention may be purified by the technique described for purifying radioiodinated secretin using talc and cellulose, as described by Boden and Chey, Endocrinology 92, 1617–24 (1973) and Boden et al, Hormone and Metabolic Research 5, 237–40 (1973). Alternatively, purification can be effected by: paper chromatoelectrophoresis; gel filtration; or thin layer chromatography. The talc and cellulose method is preferred, particularly where a significant amounts of damaged labeled compound are formed.

Radioiodinated [6-TYR] Secretin may be used for the radioimmunoassay of Secretin by procedures known in the art, e.g., as described by Boden and Chey, supra, using the radioiodinated derivative of the present invention in place of radioiodinated secretin.

The invention will be further described with respect to the following examples.

EXAMPLE II

Ten ug of 6-tyrosylsecretin in 50 ul 0.50 M phosphate buffer (pH 7.4) were treated with 7mC Na $^{125}I$. After addition of 165 ug chloramine -T in 50 ul 0.50 M phosphate buffer (pH 7.4), the mixture was agitated for 30 seconds. The iodination was stopped by the addition of 500 ug sodium metabisulfite in 50 ul buffer. Purification was effected by the method of Boden and Chey supra.

The radioiodinated [6-TYR] Secretin was evaluated by paper chromatoelectrophoresis in non-immune serum with and without added immune serum (antisecretin antiserum) as described by Boden and Chey, supra, using the radioiodinated derivative of the present invention in place of secretin $^{125}I$. Immunoreactivity and immunochemical equivalence of the radioiodinated [6-TYR] Secretin was further demonstrated by its complete displacement from antisecretin antibodies by unlabeled secretin or [6-TYR] Secretin, thereby satisfying the basic requirement for radioimmunoassays of secretin and of [6-TYR] Secretin.

In addition, specific activities of greater than 300 UC/ug were obtained.

The ability to prepare both porcine Secretin and [6-TYR] Secretin by a solid phase synthesis technique is completely unexpected in that prior attempts in this respect were not successful; note, *Secretin, Cholecystokinin, Pancreozymin and Gastrin*, Bodansky Pgs. 183–84 (1973). In addition, the fact that [6-TYR] Secretin is biologically active was completely unexpected.

Radioiodinated [6-TYR] Secretin is an improvement over radioiodinated secretin as a result of higher specific activity and improved storage stability. In addition, the radioiodinated derivative of the present invention can be produced in higher yields and at milder iodination conditions.

Numerous modifications and variations of the present invention are possible in light of the above teachings and, therefore, within the scope of the appended claims the invention may be practised otherwise than as particularly described.

We claim:

1. A compound which is a peptide selected from the group consisting of (a) [6-TYR] Secretin and its salts; and (b) 6-(radioiodinated-TYR) secretin, wherein the amino acid residues of the compound are in L-form and the radioiodine is selected from the group consisting of $^{125}I$, $^{131}I$ and $^{123}I$.

2. The compound of claim 1 wherein the peptide is [6-TYR] Secretin in L-form.

3. The compound of claim 1 wherein the peptide is 6-(radioiodinated-TYR) Secretin in L-form.

4. The compound of claim 1 wherein the compound is 6-($3^1$-iodo$^{125}I$-tyrosyl) Secretin in L-form.

5. The compound of claim 1 wherein the compound is 6-($3^1$, $5^1$-diiodo - $^{125}I_2$ - tyrosyl) Secretin in L-form.

6. The compound of claim 1 wherein the compound is 6 - ($3^1$ - iodo $^{131}I$ - tyrosyl) Secretin in L-form.

7. The compound of claim 1 wherein the compound is 6 - ($3^1$ - diiodo $^{131}I_2$ - tyrosyl) Secretin in L-form.

8. A compound of the formula:

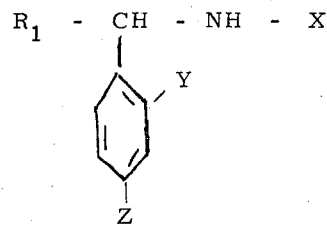

wherein $R_1$ is a solid polymer selected from the group consisting of polystyrene and polystyrene cross-linked with divinyl benzene, said polymer being linked through its phenyl ring;

Y is selected from the group consisting of hydrogen and lower alkoxy;

Z is selected from the group consisting of hydrogen, lower alkoxy and nitro, and X is selected from the group consisting of the following protected and unprotected amino acid residues, in L-form, and salts thereof, 1. TYR-THR-SER-GLU-LEU-SER-ARG-LEU-ARG-LEU-ARG-ASP-SER-ALA-ARG-LEU-GLN-ARG-LEU-LEU-GLN-GLY-LEU-VAL-
2. THR-TYR-THR-SER-GLU-LEU-SER-ARG-LEU-ARG-ASP-SER-ALA-ARG-LEU-GLN-ARG-LEU-LEU-GLN-GLY-LEU-VAL-
3. GLY-THR-TYR-THR-SER-GLU-LEU-SER-ARG-LEU-ARG-ASP-SER-ALA-ARG-LEU-GLN-ARG-LEU-LEU-GLN-GLY-LEU-VAL-
4. ASP-GLY-THR-TYR-THR-SER-GLU-LEU-SER-ARG-LEU-ARG-ASP-SER-ALA-ARG-LEU-GLN-ARG-LEU-LEU-GLN-GLY-LEU-VAL-
5. SER-ASP-GLY-THR-TYR-THR-SER-GLU-LEU-SER-ARG-LEU-ARG-ASP-SER-ALA-ARG-LEU-GLN-ARG-LEU-LEU-GLN-GLY-LEU-VAL-
6. HIS-SER-ASP-GLY-THR-TYR-THR-SER-GLU-LEU-SER-ARG-LEU-ARG-ASP-SER-ALA-ARG-LEU-GLN-ARG-LEU-LEU-GLN-GLY-LEU-VAL-
7. PHE-THR-SER-GLU-LEU-SER-ARG-LEU-ARG-ASP-SER-ALA-ARG-LEU-GLN-ARG-LEU-LEU-GLN-GLY-LEU-VAL-
8. THR-PHE-THR-SER-GLU-LEU-SER-ARG-LEU-ARG-ASP-SER-ALA-ARG-LEU-GLN-ARG-LEU-LEU-GLN-GLY-LEU-VAL-
9. GLY-THR-PHE-THR-SER-GLU-LEU-SER-ARG-LEU-ARG-ASP-SER-ALA-ARG-LEU-GLN-ARG-LEU-GLN-ARG-LEU-LEU-GLN-GLY-LEU-VAL-
10. ASP-GLY-THR-PHE-THR-SER-LEU-SER-ARG-LEU-ARG-ASP-SER-ALA-ARG-LEU-GLN-ARG-LEU-LEU-GLN-GLY-LEU-VAL-
11. SER-ASP-GLY-THR-PHE-THR-SER-GLU-LEU-SER-ARG-LEU-ARG-ASP-SER-ALA-ARG-LEU-GLN-ARG-LEU-LEU-GLN-GLY-LEU-VAL-
12. HIS-SER-ASP-GLY-THR-PHE-THR-SER-GLU-LEU-SER-ARG-LEU-ARG-ASP-SER-ALA-ARG-LEU-ARG-LEU-LEU-GLN-GLY-LEU-VAL-
13. THR-SER-GLU-LEU-SER-ARG-LEU-ARG-ASP-SER-ALA-ARG-LEU-GLN-ARG-LEU-LEU-GLN-GLY-LEU-VAL-
14. SER-GLU-LEU-SER-ARG-LEU-ARG-ASP-SER-ALA-ARG-LEU-GLN-ARG-LEU-LEU-GLN-GLY-LEU-VAL-
15. GLU-LEU-SER-ARG-LEU-ARG-ASP-SER-ALA-ARG-LEU-GLN-ARG-LEU-LEU-GLN-GLY-LEU-VAL-
16. LEU-SER-ARG-LEU-ARG-ASP-SER-ALA-ARG-LEU-GLN-ARG-LEU-LEU-GLN-GLY-LEU-VAL-
17. SER-ARG-LEU-ARG-ASP-SER-ALA-ARG-LEU-GLN-ARG-LEU-LEU-GLN-GLY-LEU-VAL-
18. ARG-LEU-ARG-ASP-SER-ALA-ARG-LEU-GLN-ARG-LEU-LEU-GLN-GLY-LEU-VAL-
19. LEU-ARG-ASP-SER-ALA-ARG-LEU-GLN-ARG-LEU-LEU-GLN-GLY-LEU-VAL-
20. ARG-ASP-SER-ALA-ARG-LEU-GLN-ARG-LEU-LEU-GLN-GLY-LEU-VAL-
21. ASP-SER-ALA-ARG-LEU-GLN-ARG-LEU-LEU-GLN-GLY-LEU-VAL-
22. SER-ALA-ARG-LEU-GLN-ARG-LEU-LEU-GLN-GLY-LEU-VAL-
23. ALA-ARG-LEU-GLN-ARG-LEU-LEU-GLN-GLY-LEU-VAL-
24. ARG-LEU-GLN-ARG-LEU-LEU-GLN-GLY-LEU-VAL-
25. LEU-GLN-ARG-LEU-LEU-GLN-GLY-LEU-VAL-
26. GLN-ARG-LEU-LEU-GLN-GLY-LEU-VAL-
27. ARG-LEU-LEU-GLN-GLY-LEU-VAL-
28. LEU-LEU-GLN-GLY-LEU-VAL-
29. LEU-GLN-GLY-LEU-VAL-
30. GLN-GLY-LEU-VAL-
31. GLY-LEU-VAL-
32. GLY-LEU-VAL-
33. LEU-VAL- 9. The compound of claim 8 wherein X is selected from the group consisting of protected and unprotected, HIS-SER-ASP-GLY-THR-TYR-THR-SER-GLU-LEU-SER-ARG-LEU-ARG-ASP-SER-ALA-ARG-LEU-GLN-ARG-LEU-LEU-GLN-GLY-LEU-VAL- 10. The compound of claim 8 wherein X is selected from the group consisting of protected and unprotected HIS-SER-ASP-GLY-THR-PHE-THR-SER-GLU-LEU-SER-ARG-LEU-ARG-ASP-SER-ALA-ARG-LEU-GLN-ARG-LEU-LEU-GLN-GLY-LEU-VAL- 11. The compound of claim 9 wherein the peptide is unprotected.

12. The compound of claim 10 wherein the peptide is unprotected.

13. The compound of claim 11 wherein Y and Z are hydrogen.

14. The compound of claim 12 wherein Y and Z are hydrogen.

15. The compound of claim 9 wherein the guanidine group of ARG is protected with a guanidine protecting group, the hydroxyl groups of SER, THR and TYR are protected with hydroxyl protecting groups, the carboxyl groups of ASP and GLU protected by carboxyl protecting groups, GLY, LEU, ALA, GLN and VAL are unprotected and HIS is selected from the group consisting of unprotected HIS, amino protected HIS, imidazole protected HIS and amino and imidazole protected HIS.

16. The compound of claim 10 wherein the guanidine group of ARG is protected with a guanidine protecting group, the hydroxyl groups of SER and THR are protected with hydroxyl protecting groups, the carboxyl groups of ASP and GLU protected by carboxyl protecting groups, GLY, LEU, PHE, ALA, GLN and VAL are unprotected and HIS is selected from the group consisting of unprotected HIS, amino protected HIS, imidazole protected HIS and amino and imidazole protected HIS.

* * * * *

UNITED STATES PATENT OFFICE
CERTIFICATE OF CORRECTION

Patent No. 3,987,014  Dated October 19, 1976

Inventor(s) MARIANO GUIDUCCI et al.

It is certified that error appears in the above-identified patent and that said Letters Patent are hereby corrected as shown below:

Column 1, line 5, delete "[6-IVR]" and insert --[6-TYR]--;

Column 7, line 9, Compound 1 - delete "-LEU-ARG".

Signed and Sealed this

Fifteenth Day of February 1977

[SEAL]

Attest:

RUTH C. MASON
*Attesting Officer*

C. MARSHALL DANN
*Commissioner of Patents and Trademarks*